United States Patent
Dave et al.

(10) Patent No.: US 8,343,169 B2
(45) Date of Patent: Jan. 1, 2013

(54) SURGICAL INSTRUMENT

(76) Inventors: Amar L. Dave, Ottawa, IL (US); Roop K. Dave, Ottawa, IL (US)

(*) Notice: Subject to any disclaimer, the term of this patent is extended or adjusted under 35 U.S.C. 154(b) by 138 days.

(21) Appl. No.: 12/844,115

(22) Filed: Jul. 27, 2010

(65) Prior Publication Data

US 2012/0029527 A1 Feb. 2, 2012

(51) Int. Cl.
*A61B 17/32* (2006.01)

(52) U.S. Cl. ........................ 606/118

(58) Field of Classification Search .......... 606/118–120, 606/131, 157
See application file for complete search history.

(56) References Cited

U.S. PATENT DOCUMENTS

| | | | |
|---|---|---|---|
| 5,797,921 A * | 8/1998 | Cimini et al. | 606/118 |
| 7,303,567 B1 * | 12/2007 | Smith | 606/118 |
| 7,591,824 B2 | 9/2009 | Dave | |
| 2004/0215210 A1 * | 10/2004 | Duel | 606/118 |
| 2007/0060928 A1 * | 3/2007 | Dave et al. | 606/118 |

* cited by examiner

*Primary Examiner* — Elizabeth Houston
(74) *Attorney, Agent, or Firm* — James Ray & Assoc

(57) ABSTRACT

A surgical instrument for performing circumcision includes a hollow body having each of an anterior open end and an axially opposed posterior open end. A dome shaped member is attached to or formed integral with the anterior end of the hollow body and has a generally semispherical shape. At least one aperture is formed through a wall of the dome shaped member and is sized to pass urine therethrough. An elongated handle is centered on the longitudinal axis and has a portion thereof positioned adjacent a juncture with one of the anterior end of the hollow body and the apex of the dome shaped member being weaker than any other portion of the body or the generally dome shaped member, whereby a reciprocation of the elongated handle causes the elongated handle to fracture at the juncture and become detached from the hollow body or the generally dome shaped member.

18 Claims, 3 Drawing Sheets

SURGICAL INSTRUMENT

CROSS-REFERENCE TO RELATED APPLICATIONS

This application is closely related to Non-Provisional patent application Ser. No. 11/521,421 filed on Sep. 14, 2006 and issued as a regular U.S. Pat. No. 7,591,824 on Sep. 22, 2009.

FIELD OF THE INVENTION

The present invention relates, in general, to surgical instruments and, more particularly, this invention relates to a surgical instrument for performing circumcisions yet, more particularly, the instant invention relates to a surgical instrument for performing circumcision that prevents sliding motion of the hollow body after the handle has been detached therefrom.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISC APPENDIX

N/A

BACKGROUND OF THE INVENTION

As is generally well known, a Plastibell surgical instrument is often used to circumcise infant boys. Plastibell surgical instrument essentially includes a conical hollow body with a pair of axially spaced open and a handle attached to one end of the hollow body and designed for fracture and subsequently detachment at juncture therewith. It has been found that Plastibell surgical instruments currently in use, including the one described and taught in U.S. Pat. No. 7,591,824 issued on Sep. 22, 2009 and owned by the inventors of the instant invention, may, due to open ends, slide along the penile member after the handle is detached, potentially causing complications after procedure and/or injury to the infant boy.

Therefore, there is a need for an improved surgical instrument for performing circumcision that prevents sliding motion of the hollow body after the handle has been detached therefrom.

SUMMARY OF THE INVENTION

The invention provides a surgical instrument for performing circumcision. The surgical instrument includes a hollow body having each of an anterior open end and a posterior open end spaced apart from the anterior end along a longitudinal axis of the surgical instrument. A generally dome shaped member is attached to or formed integral with the anterior end of the hollow body. The generally dome shaped member has each of a generally semispherical shape, a generally open end thereof disposed on the anterior end of the body and an apex extending outwardly from the anterior end along the longitudinal axis. At least one aperture is formed through a wall of the generally dome shaped member and sized to pass urine therethrough. An elongated handle is centered on the longitudinal axis and has a portion thereof positioned adjacent a juncture with one of the anterior end of the hollow body and the apex of the generally dome shaped member being weaker than any other portion of the one of body and the generally dome shaped member. A reciprocation of the elongated handle causes the elongated handle to fracture at the juncture and become detached from the one of hollow body and the generally dome shaped member.

OBJECTS OF THE INVENTION

It is, therefore, one of the primary objects of the present invention to provide an improved surgical instrument for performing circumcision that prevents sliding motion of the hollow body after the handle has been detached therefrom.

Another object of the present invention is to provide an improved surgical instrument for performing circumcision that has a dome shaped member attached to one end of the hollow body and preventing sliding motion of the hollow body after the handle has been detached therefrom.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE VARIOUS EMBODIMENTS OF THE INVENTION

Figure 1:
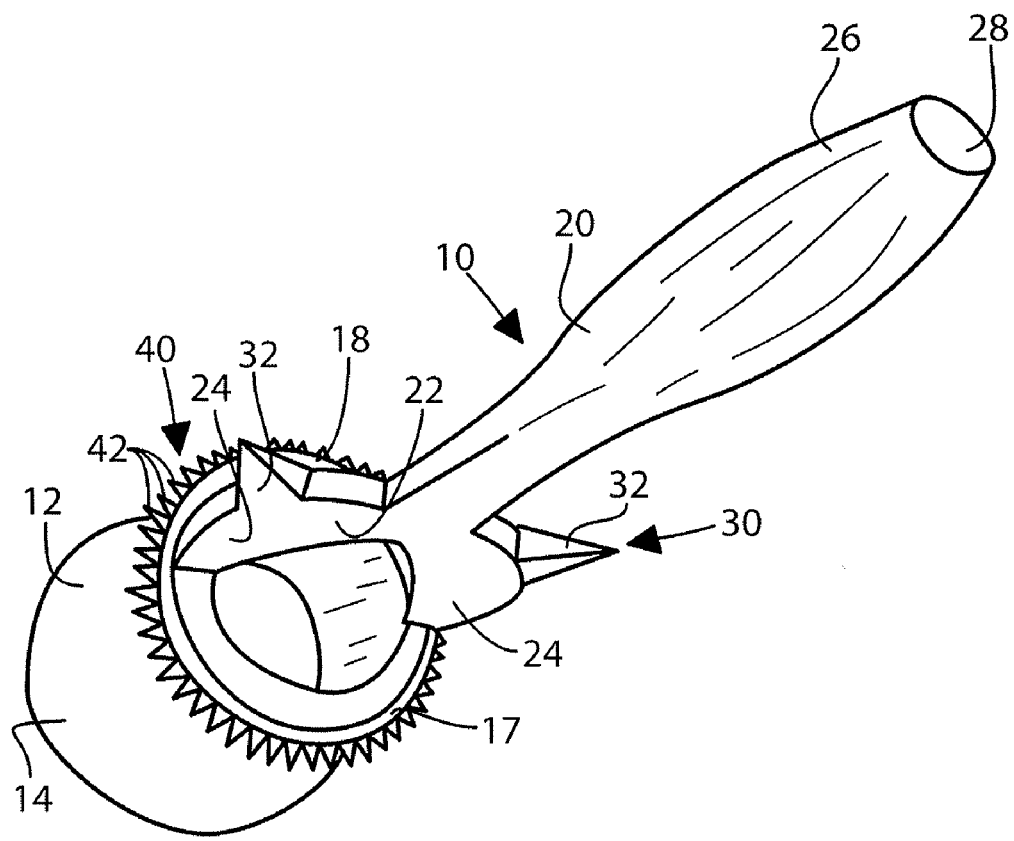
FIG. 1 is a perspective view of a prior art surgical instrument for performing circumcisions.

Prior to proceeding to the more detailed description of the present invention, it should be noted that, for the sake of clarity and understanding, identical components which have identical functions have been identified with identical reference numerals throughout the several views illustrated in the drawing figures.

The instant invention is illustrated and described in combination with a surgical instrument taught in a related U.S. Pat. No. 7,591,824 on Sep. 22, 2009 owned by the inventors of the instant invention and incorporated by reference into this document, although it will be apparent to those skilled in the relevant art that the present invention may be applied to other similar surgical instruments for performing circumcision and as such should not be interpreted as a limiting factor of the instant invention.

Reference is now made, to FIG. 1, labeled as prior art, and showing a surgical instrument 10 taught in a related U.S. Pat. No. 7,591,824 issued on Sep. 22, 2009 and owned by the inventors of the instant invention. Such surgical instrument 10 includes a body 12, a handle 20, a pair of barbs 32 and foreskin excising means 40. The detail description of this prior art surgical instrument will be omitted in this document for the sake of brevity.

Now in a particular reference to FIGS. 2-5, therein is shown an improved surgical instrument, generally designated as 100, for performing circumcision.

The surgical instrument 100 includes a hollow body 12 which is open at both ends thereof. The body 12 includes an interior surface 16 thereof being conically shaped and tapered to define an enlarged opening at a posterior end 14 of the body 12. As it is well known, the device 10 includes an annular flange 17 which is secured to an exterior surface of the body 12 adjacent to and spaced from the anterior end 18 thereof.

The surgical instrument 100 further includes a generally dome shaped member 110 attached to or formed integral with the anterior end 18 of the hollow body 12. The generally dome shaped member 110 is defined by a generally semispherical shape and has a generally open end 112 thereof disposed on the anterior end 18 of the hollow body 12 and an apex 114 thereof extending outwardly from the anterior end 18 of the hollow body 12 along the longitudinal axis 13 of the surgical instrument 100.

At least one aperture 120 is formed through a wall of the generally dome shaped member 110 and is sized to pass urine therethrough.

Figure 2:
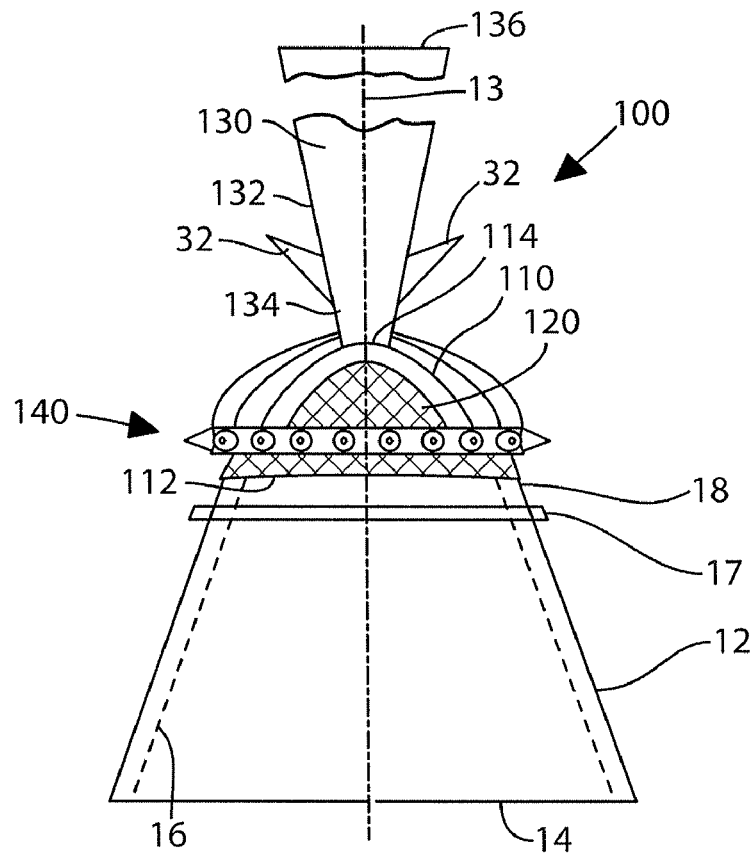
FIG. 2 is an elevation view of a surgical instrument for performing circumcisions and constructed in accordance with embodiments of the instant invention.

Now in a particular reference to FIG. 2, an elongated handle 130 is centered on the longitudinal axis 13 and has a portion 134 thereof positioned adjacent a juncture with one of the anterior end 18 of the hollow body 12 and the apex 114 of the generally dome shaped member 110 being weaker than any other portion of the one of hollow body 12 or the generally dome shaped member 110, whereby a reciprocation of the elongated handle 130 causes the elongated handle 130 to fracture at the juncture and become detached from such one of hollow body 12 or from the generally dome shaped member 110.

Thus, it will be understood, that the dome shaped member 110 provides means for preventing sliding motion of the hollow body 12 in a direction along the longitudinal axis 13 toward the base of the penile member (not shown) after the elongated handle 130 has been detached.

The portion 134 of the elongated handle 130 disposed adjacent the juncture with the apex 114 of the generally dome shaped member 110 is being thinner than any other portion of the elongated handle 130.

The distal end 136 of the elongated handle 130 has each of a round shape and a planar surface for aiding in separating the foreskin from penile glans (not shown).

In further reference to FIG. 2, each of the pair of barbs 32 that was previously attached to one leg 24 of the Y-shaped handle 20 has been repositioned and now has a proximal end thereof disposed stationary on and extending outwardly from the exterior surface or edge 132 of the elongated handle 130 and a pointed distal end thereof spaced from the exterior surface or edge 132. As previously taught, each of the pair of barbs 32 is pointed at a predetermined angle relative to the longitudinal axis 13 away from the anterior end 18 of the hollow body 12, wherein a height of the each of the pair of pointed barbs 32 is sufficient to puncture a wall of a foreskin.

The surgical instrument 100 additionally includes means, generally designated as 140, attached to the elongated handle 130 for excising a distal portion of the foreskin (not shown).

Figure 3:
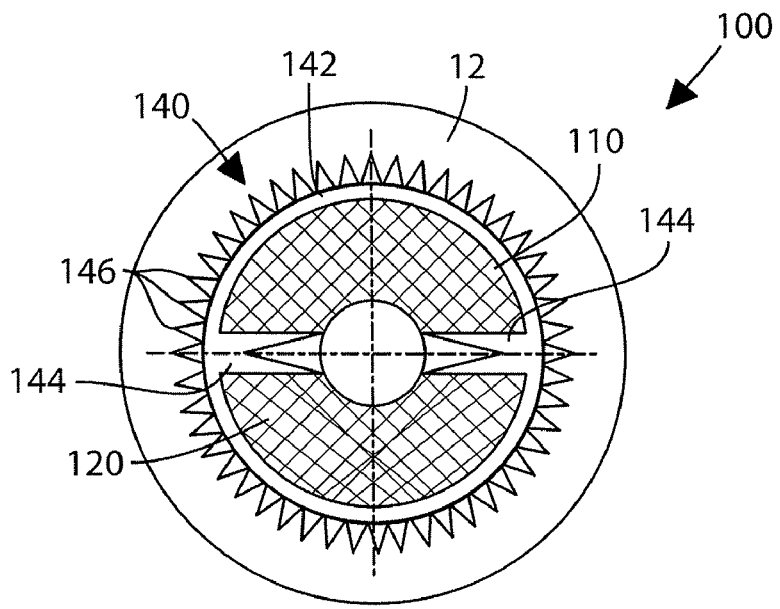
FIG. 3 illustrates a planar view of the surgical instrument of FIG. 2.

In further reference to FIGS. 2-3, the foreskin excising means 140 includes an annular flange 142 positioned in close proximity to the anterior end 18 of the hollow body 12, an arrangement, for example such as a pair of elongated members 144, attaching the annular flange 142 to the elongated handle 130 and a plurality of outwardly extending pointed barbs 146 disposed, in a plane transverse to the longitudinal axis 13 on an outer edge of the annular ring 142. The pointed barbs 146 are preferably formed integral with the annular flange 142.

Figure 4:
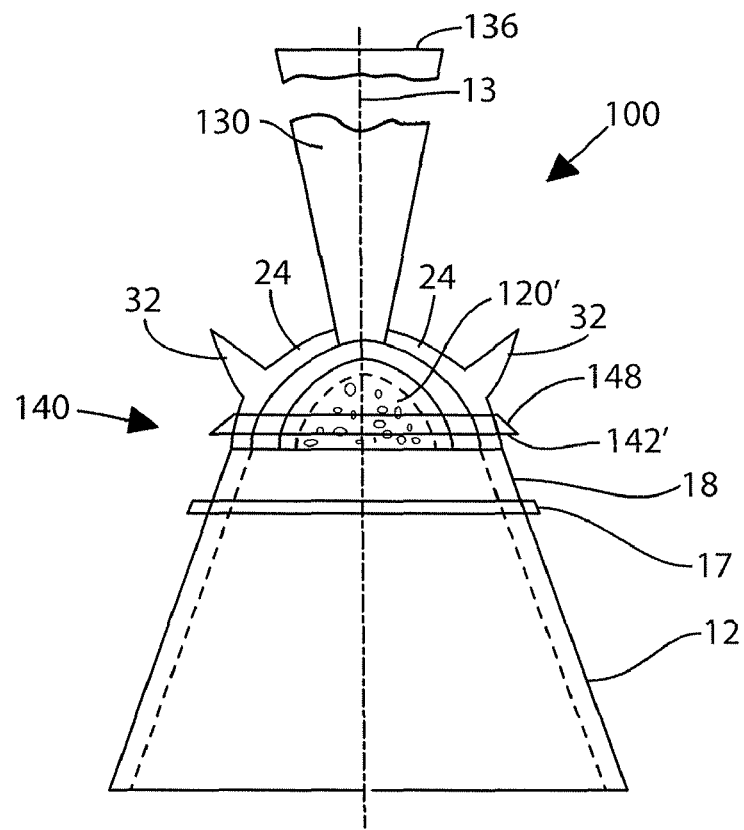
FIG. 4 is another elevation view of the surgical instrument of the instant invention for performing circumcisions.

Now in reference to FIG. 4, the foreskin excising means 140 is shown as including the annular flange 142' positioned in close proximity to the anterior end 18 of the hollow body 12, the annular flange 142' having a surface 148 thereof tapering inwardly toward the anterior end 18 of the hollow body 12.

In further reference to FIG. 3, the elongated handle 130 is shown as including a pair of legs 24, each leg 24 having each of a proximal end thereof secured to the elongated handle 130 and a distal end thereof secured to one of two diametrically opposed points on the anterior end 18 and of the hollow body 12, the distal end being weaker than any other portion of the hollow body 12, wherein the generally dome shaped member 110 is disposed between the pair of legs 24 and whereby a reciprocation of the elongated handle 130 causes the elongated handle 130 to fracture at the distal end of the each leg 24 and become detached from the hollow body 12. When the elongated handle 130 is provided with a pair of legs 24, each barb 32 is disposed on a respective leg 24. Furthermore, the foreskin excising means 140 is attached directly to the legs 24.

Attachment of the foreskin excising means 140 directly to the legs 24 or to the elongated handle 130 has been found advantageous is preventing any unintentional and potential injury after the elongated handle 130 has been detached from the hollow body 12, since the foreskin excising means 140 will be removed together with the elongated handle 130.

The at least one aperture 120 is preferably a plurality of apertures 120 formed through a wall of the dome shaped member 110. Such plurality of apertures 120 may be sized and configured so as to result in a mesh appearance of the dome shaped member 110, as best shown in FIGS. 2-3.

The plurality of apertures 120' may also have a round shapes as best shown in FIG. 4.

Figure 5:
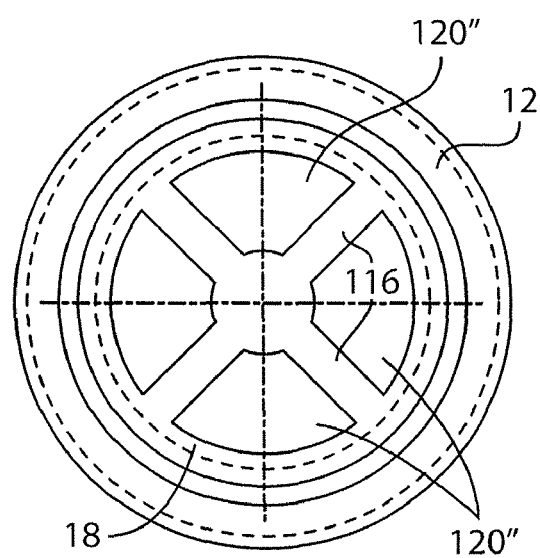
FIG. 5 illustrates another planar view of the surgical instrument with the handle detached from the hollow body.

The plurality of apertures may be also provided as a quartet of generally triangular shaped apertures 120' formed through a wall of the dome shaped member 110 and equally spaced from each other on an exterior surface of the dome shaped member 110, as best shown in FIG. 5. One edge of each generally triangular shaped aperture 120" is disposed on the anterior end 18 of the hollow body 12, thus essentially defining the dome shaped member 110 by a pair of arches 116 disposed generally perpendicular to each other.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

We claim:

1. A surgical instrument for performing circumcision, said instrument comprising:

(a) a hollow body having each of an anterior open end and a posterior open end spaced apart from said anterior end along a longitudinal axis of said surgical instrument;

(b) a generally dome shaped member attached to or formed integral with said anterior end of said hollow body, said generally dome shaped member having each of a generally semispherical shape, a generally open end thereof disposed on said anterior end of said body and an apex extending outwardly from said anterior end along said longitudinal axis;

(c) a plurality of apertures formed in a predetermined pattern through a wall of said generally dome shaped member and sized to pass urine therethrough; and (d) an elongated handle centered on said longitudinal axis and having a portion thereof positioned adjacent a juncture with one of said anterior end of said hollow body and said apex of said generally dome shaped member being weaker than any other portion of said one of body and said generally dome shaped member, whereby a reciprocation of said elongated handle causes said elongated handle to fracture at said juncture and become detached from said one of hollow body and said generally dome shaped member.

2. The surgical instrument of claim 1, further comprising a pair of barbs.

3. The surgical instrument, according to claim 2, wherein each of said pair of barbs is disposed stationary on and extending outwardly from an exterior surface or edge of said elongated handle, said each barb having each of a proximate end thereof rigidly positioned on said exterior surface or edge, a pointed distal end thereof spaced from said exterior surface or edge and a plurality of triangular shaped side surfaces connecting said pointed distal end with said proximate end, wherein said each of said pair of barbs is pointed at a predetermined angle relative to said longitudinal axis away from said anterior end of said hollow body, and wherein a height of said each of said pair of pointed barbs is sufficient to puncture a wall of a foreskin.

4. The surgical instrument, according to claim 1, wherein said portion of said elongated handle positioned adjacent said juncture includes a pair of legs, each leg having each of a proximal end thereof secured to said elongated handle and a distal end thereof secured to one of two diametrically opposed points on said anterior end and of said hollow body, said distal end being weaker than any other portion of said hollow body, wherein said generally dome shaped member is disposed between said pair of legs and whereby a reciprocation of said handle causes said handle to fracture at said distal end of said each leg and become detached from said hollow body.

5. The surgical instrument of claim 4, further including a pair of barbs, each of said pair of barbs disposed stationary on and extending outwardly from an exterior curved edge of a respective leg, said each barb having each of a proximate end thereof rigidly positioned on said exterior curved edge, a pointed distal end thereof spaced from said curved edge and a plurality of triangular shaped side surfaces connecting said pointed distal end with said proximate end, wherein said each of said pair of barbs is pointed at a predetermined angle relative to said longitudinal axis away from said anterior end of said hollow body, and wherein a height of said each of said pair of pointed barbs is sufficient to puncture a wall of a foreskin.

6. The surgical instrument, according to claim 1, wherein said portion of said elongated handle disposed adjacent said juncture with said apex of said generally dome shaped member is being thinner than any other portion of said elongated handle.

7. The surgical instrument, according to claim 1, wherein a distal end of said elongated handle has each of a round shape and a planar surface for aiding in separating the foreskin from penile glans.

8. The surgical instrument of claim 1, further including means attached to said handle for excising a distal portion of the foreskin.

9. The surgical instrument, according to claim 8, wherein said foreskin excising means includes an annular flange positioned in close proximity to said anterior end of said hollow body, an arrangement attaching said annular flange to said elongated handle and a plurality of outwardly extending pointed barbs disposed, in a plane transverse to said longitudinal axis, on an outer edge of said annular flange.

10. The surgical instrument of claim 1, wherein said predetermined pattern defines mesh appearance of said plurality of apertures.

11. The surgical instrument of claim 1, wherein said predetermined pattern defines a quartet of generally triangular shaped apertures formed through said wall of said generally dome shaped member and equally spaced from each other on an exterior surface of said dome shaped member.

12. The surgical instrument, according to claim 11, wherein one edge of each generally triangular shaped aperture is disposed on said anterior end of said hollow body.

13. A surgical instrument for performing circumcision, said instrument comprising:

(a) a hollow body open at both ends thereof;

(b) a Y-shaped handle having an elongated member and a pair of legs disposed on a proximate end of said elongated member and positioned adjacent an anterior end of said body, each leg having distal end thereof secured to one of two diametrically opposed points on said anterior end, said each leg having a portion thereof disposed adjacent a juncture with said anterior end of said body being weaker than any other portion of said body, whereby a reciprocation of said handle causes said handle to fracture at each juncture and become detached from said body;

(c) a pair of barbs, each of said pair of barbs disposed stationary on and extending outwardly from an exterior curved edge of a respective leg, said each barb having each of a proximate end thereof rigidly positioned on said exterior curved edge, a pointed distal end thereof spaced from said curved edge and a plurality of triangular shaped side surfaces connecting said pointed distal end with said proximate end, wherein said each of said pair of barbs is pointed at a predetermined angle relative to a longitudinal axis of said elongated member away from said anterior end of said hollow body, and wherein a height of said each of said pair of pointed barbs is sufficient to puncture a wall of a foreskin;

(d) a generally dome shaped member attached to or formed integral with said anterior end of said hollow body, said generally dome shaped member having each of a generally semispherical shape, a generally open end thereof disposed on said anterior end of said body and an apex extending outwardly from said anterior end along said longitudinal axis; and (e) a plurality of apertures formed through a wall of said generally dome shaped member and defining mesh appearance thereof.

14. The surgical instrument of claim 13, further including means attached to said handle for excising a distal portion of said foreskin.

15. The surgical instrument, according to claim 14, wherein said foreskin excising means includes an annular flange positioned in close proximity to said anterior end of said hollow body, an arrangement attaching said annular flange to one of said pair of legs and said elongated member and a plurality of outwardly extending pointed barbs disposed, in a plane transverse to said longitudinal axis on an outer edge of said annular flange.

16. The surgical instrument, according to claim 14, wherein said plurality of pointed barbs are formed integral with said annular flange.

17. The surgical instrument, according to claim 14, wherein said foreskin excising means includes an annular flange positioned in close proximity to said anterior end of said hollow body, said annular flange having a one surface thereof tapering inwardly toward said anterior end of said body and an arrangement attaching said annular flange to one of said pair of legs and said elongated member.

18. A surgical instrument for performing circumcision, said instrument comprising:
(a) a hollow body open at both ends thereof;
(b) a Y-shaped handle having an elongated member and a pair of legs disposed on a proximate end of said elongated member and positioned adjacent an anterior end of said body, each leg having distal end thereof secured to one of two diametrically opposed points on said anterior end, said each leg having a portion thereof disposed adjacent a juncture with said anterior end of said body being weaker than any other portion of said body, whereby a reciprocation of said handle causes said handle to fracture at each juncture and become detached from said body;
(c) a pair of barbs, each of said pair of barbs disposed stationary on and extending outwardly from an exterior curved edge of a respective leg, said each barb having each of a proximate end thereof rigidly positioned on said exterior curved edge, a pointed distal end thereof spaced from said curved edge and a plurality of triangular shaped side surfaces connecting said pointed distal end with said proximate end, wherein said each of said pair of barbs is pointed at a predetermined angle relative to a longitudinal axis of said elongated member away from said anterior end of said hollow body, and wherein a height of said each of said pair of pointed barbs is sufficient to puncture a wall of a foreskin;
(d) a generally dome shaped member attached to or formed integral with said anterior end of said hollow body, said generally dome shaped member having each of a generally semispherical shape, a generally open end thereof disposed on said anterior end of said body and an apex extending outwardly from said anterior end along said longitudinal axis; and
(e) a quartet of apertures formed through a wall of said generally dome shaped member and equally spaced from each other on said dome shaped member.

* * * * *